(12) United States Patent
Fletcher et al.

(10) Patent No.: US 8,069,135 B2
(45) Date of Patent: Nov. 29, 2011

(54) SYSTEMS AND METHODS FOR A PREDICTIVE NOTIFICATION ENGINE

(75) Inventors: Robert C. Fletcher, Cary, IL (US);
Anthony Ricamato, West Chicago, IL (US); Brian Fors, Barrington, IL (US);
Eric Jester, Hoffman Estates, IL (US);
Mark Wilhelm, Palatine, IL (US)

(73) Assignee: General Electric Company, Schenectady, NY (US)

( * ) Notice: Subject to any disclaimer, the term of this patent is extended or adjusted under 35 U.S.C. 154(b) by 904 days.

(21) Appl. No.: 12/051,974

(22) Filed: Mar. 20, 2008

(65) Prior Publication Data

US 2009/0240651 A1   Sep. 24, 2009

(51) Int. Cl.
*G06F 15/00* (2006.01)
*G06F 15/18* (2006.01)

(52) U.S. Cl. ............... 706/62; 706/45; 706/46; 706/47; 706/52; 600/300; 600/301; 600/411

(58) Field of Classification Search ................. None
See application file for complete search history.

(56) References Cited

U.S. PATENT DOCUMENTS

| | | | |
|---|---|---|---|
| 4,197,854 A | 4/1980 | Kasa | |
| 5,199,439 A | 4/1993 | Zimmerman et al. | |
| 5,724,983 A * | 3/1998 | Selker et al. | 600/301 |
| 6,024,699 A * | 2/2000 | Surwit et al. | 600/300 |
| 6,246,992 B1 * | 6/2001 | Brown | 705/2 |
| 7,256,708 B2 * | 8/2007 | Rosenfeld et al. | 340/870.01 |
| 7,433,853 B2 * | 10/2008 | Brockway et al. | 706/45 |
| 2002/0120187 A1 * | 8/2002 | Eiffert et al. | 600/407 |
| 2006/0047538 A1 * | 3/2006 | Condurso et al. | 705/3 |
| 2007/0060797 A1 * | 3/2007 | Ball et al. | 600/300 |
| 2007/0080223 A1 * | 4/2007 | Japuntich | 235/439 |
| 2007/0094227 A1 | 4/2007 | Randazzo et al. | |
| 2008/0269625 A1 * | 10/2008 | Halperin et al. | 600/508 |
| 2008/0269631 A1 * | 10/2008 | Denison et al. | 600/544 |

* cited by examiner

*Primary Examiner* — Omar Fernandez Rivas
(74) *Attorney, Agent, or Firm* — McAndrews, Held & Malloy, Ltd.; Armando Pastrana, Jr.

(57) ABSTRACT

Certain embodiments of the present invention provide a system for predictive notification including a notification engine adapted to receive a sequence of data values for a parameter from a medical device. The notification engine is adapted to determine a prediction based at least in part on the sequence of data values. The notification engine is adapted to generate a notification based on the prediction.

16 Claims, 4 Drawing Sheets

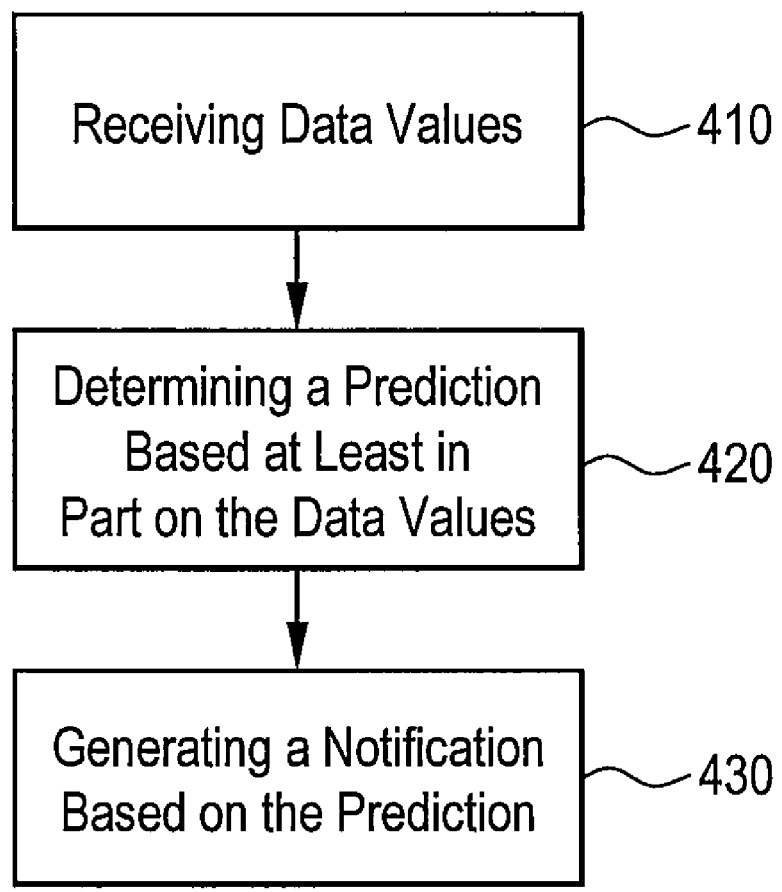

US 8,069,135 B2

SYSTEMS AND METHODS FOR A PREDICTIVE NOTIFICATION ENGINE

RELATED APPLICATIONS

[Not Applicable]

FEDERALLY SPONSORED RESEARCH OR DEVELOPMENT

[Not Applicable]

MICROFICHE/COPYRIGHT REFERENCE

[Not Applicable]

BACKGROUND OF THE INVENTION

The present invention generally relates to notification in a healthcare environment. In particular, the present invention relates to systems and methods for a predictive notification engine.

Medical devices include devices such as physiological monitors, infusion pumps, ventilators, oximeters, fetal monitors, lab instruments, portable vitals measuring equipment, warmers, and dialysis machines. Medical devices are important to the practice of modern medicine. For example, in a hospital intensive care unit (ICU), a variety of medical devices may surround each patient, each performing an important task. A patient connected to one or more vital-signs monitors may also be receiving drugs or other fluids under the control of an infusion pump, for example. In some cases, a patient may have some of their physiological processes supported by medical devices such as ventilators.

Medical devices are able to provide data for parameters. Certain medical devices may provide a stream or sequence of values (data) for one or more parameters. For example, an electrocardiogram may provide a stream of values for the heart rate parameter, each value provided once per second or as a waveform. The parameter value may be provided simply as a data value on a wire or communicated using a simple, proprietary protocol, for example.

Parameter data from a medical device is distinct from messages from clinical applications in an information system. As discussed above, parameter data is a value (or set of values) provided from a medical device corresponding to a particular parameter. Often, the parameter data may be communicated simply as a value, without additional information or context, using a wire protocol or other similar mechanism. In contrast, messages are packages of higher-level information, typically generated by software applications in a healthcare information system. For example, a pharmacy system may provide a message to a medication management application including details such as patient identifier, medication names, and dosage rates. As another example, a clinical decision support system may receive message from an order entry system to monitor for drug interactions. Messages may be communicated using protocols such as HL7.

Current systems allow a healthcare provider to be notified when a parameter value changes in a particular way. That is, when an event occurs, a notification is generated. For example, if a ventilator detects that it has come unplugged, a notification, such as an alarm tone or light, may be desired. As another example, if a heart rate drops below a threshold, a notification is generated.

In current systems, notification mechanisms are hard-coded to the medical devices and do not allow for the creation of new notifications based on multiple parameters. In addition, current systems do not allow for creating notifications based on information gathered from separate sources. Further, as discussed above, current systems react only to events that have already occurred.

BRIEF SUMMARY OF THE INVENTION

Certain embodiments of the present invention provide a system for predictive notification including a notification engine adapted to receive a sequence of data values for a parameter from a medical device. The notification engine is adapted to determine a prediction based at least in part on the sequence of data values. The notification engine is adapted to generate a notification based on the prediction.

Certain embodiments of the present invention provide a method for predictive notification including receiving a sequence of data values for a parameter from a medical device, determining a prediction based at least in part on the sequence of data values, and generating a notification based on the prediction.

Certain embodiments of the present invention provide a computer-readable medium including a set of instructions for execution on a computer, the set of instructions including a data reception routine configured to receive a sequence of data values for a parameter from a medical device, a prediction processing routine configure to determine a prediction based at least in part on the sequence of data values, and a notification routine configured to generate a notification based on the prediction.

BRIEF DESCRIPTION OF SEVERAL VIEWS OF THE DRAWINGS

FIG. 4 illustrates a flow diagram for a method for predictive notification according to an embodiment of the present invention.

Figure 1:
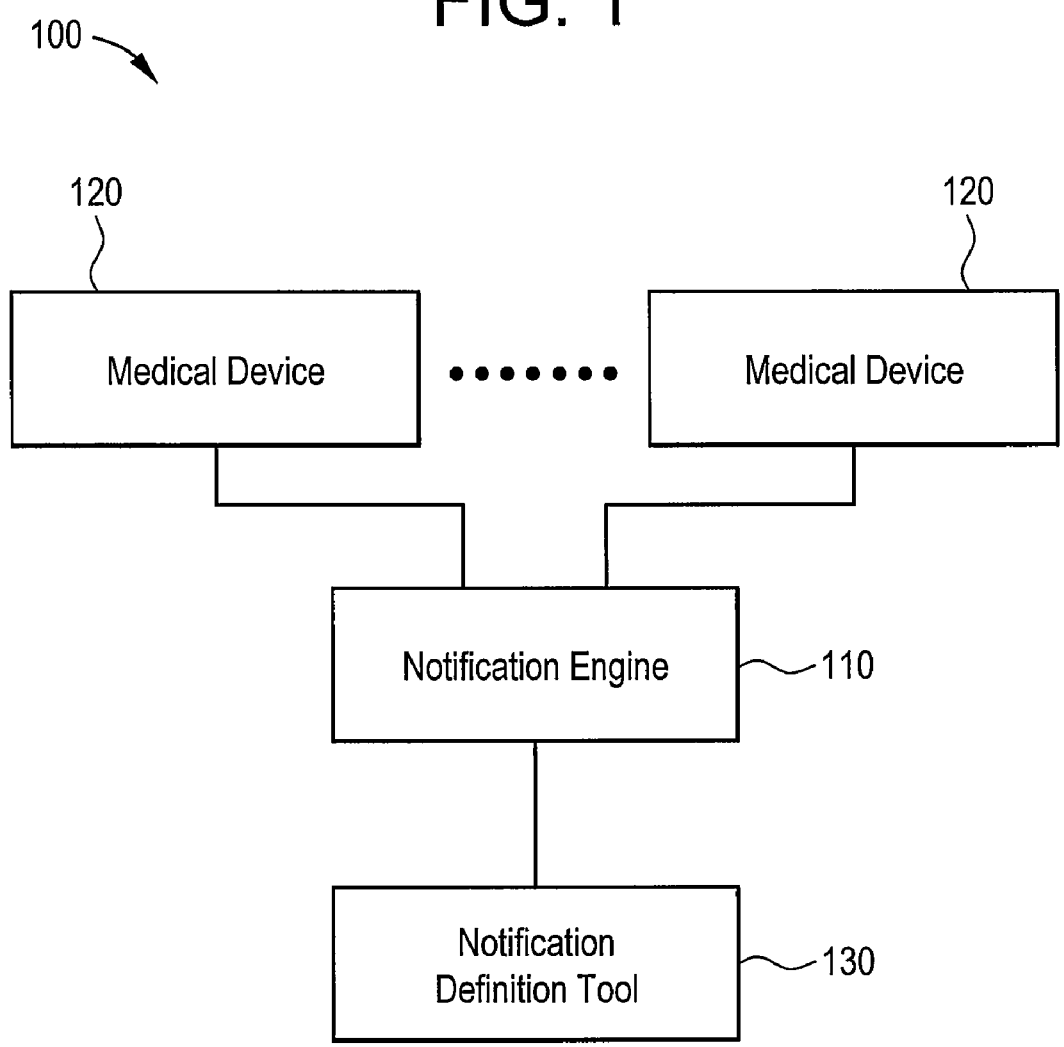
FIG. 1 illustrates a block diagram of a predictive notification system according to an embodiment of the present invention.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

Certain embodiments of the present invention provide systems and methods for a predictive notification engine. Certain embodiments provide notification based on information from multiple sources. Certain embodiments allow the prediction of a medical problem based on trends of the currently available variables. Certain embodiments allow multiple levels of notification based on the experience of a medical practitioner. Certain embodiments provide for user-defined notifications.

FIG. 1 illustrates a block diagram of a predictive notification system 100 according to an embodiment of the present invention. The system 100 includes a predictive notification engine 110, one or more medical devices 120, and a notification definition tool 130.

The notification engine 110 is in communication with the medical devices 120 and the notification definition tool 130.

In operation, a medical device 120 generates a stream or sequence of data values for a parameter. The sequence of parameter values is received by the notification engine 110. The notification engine 110 processes the sequence of parameter values based on a predictive algorithm to determine a prediction. The predictive algorithm may be specified by a user using the notification definition tool 130. Based on the prediction, a notification is generated by the notification engine 110.

A medical device 120 may include devices such as physiological monitors, infusion pumps, ventilators, oximeters, fetal monitors, lab instruments, portable vitals measuring equipment, warmers, dialysis machines, gas monitors, and gas agent monitors.

Each medical device 120 is adapted to provide data for a parameter. In certain embodiments, a medical device 120 may provide data for more than one parameter. Certain medical devices may provide a sequence of parameter values. For example, an electrocardiogram may provide a sequence of values for the heart rate parameter, each value provided once per unit of time (e.g., per second) or as a waveform. The parameter value may be provided simply as a data value on a wire or communicated using a simple, proprietary protocol, for example. In some medical devices, the form of a parameter is particular to the medical device.

The notification engine 110 is adapted to determine a prediction based at least in part on the parameter values received from the medical devices 120. The prediction may be determined by a predictive algorithm, for example. For example, the notification engine 110 may include a predictive algorithm that is executed when parameter data is received from the medical devices 120. The predictive algorithm may determine a trend based on one or more parameters. The predictive algorithm may utilize trending analysis and/or evaluating a trend over time, for example. The predictive algorithm may then determine that at some point in the future, the determined trend would indicate the occurrence of an event. Based on this determination, the notification engine 110 may provide a notification. For example, the predictive algorithm may determine that there is a trend in a blood pressure parameter that might lead to cardiac arrest in 5 minutes if not addressed. The notification engine 110 may then notify a healthcare provider of this trend and timeframe. As another example, the predictive algorithm may determine that a trend that a parameter representing the amount or concentration of a gas agent is increasing or at a maintained level while simultaneously determining that a blood pressure parameter is trending downward. These trends may, in turn, be used to determine a trend indicative of a potential heart attack, for example. The notification engine 110 may then notify a healthcare provider based on the prediction of the potential heart attack.

In certain embodiments, the predictive algorithm is specified by a user using the notification definition tool 130. For example, a user may utilize the notification definition tool 130 to create and/or develop a predictive algorithm to be provided to the notification engine 110. The notification engine 110, in turn, may then execute the predictive algorithm based on the received parameter data and, when indicated by the algorithm, provide a notification. The notification definition tool 130 may allow the user to specify complex algorithms, for example. In certain embodiments, the notification definition tool 130 is adapted to allow the creation and development of default standard-of-care predictive protocols. In certain embodiments, the notification definition tool 130 is adapted to allow the creation and development of patient-specific predictive protocols. These patient-specific protocols may be developed "on the fly." For example, a patient-specific protocol may be developed while care is being provided to the patient based on conditions discovered during the care. In certain embodiments, the predictive algorithm covers only a single phase of care. In certain embodiments, the predictive algorithm covers more than one phase of care. In certain embodiments, the predictive algorithm created and/or developed with the notification engine 110 is based on a template.

In certain embodiments, the prediction algorithm determines a prediction based at least in part on data for multiple parameters. The parameters may be from one or more medical devices 120, for example.

In certain embodiments, the prediction algorithm determines a prediction based at least in part on data from a clinical application. In certain embodiments, the prediction algorithm determines a prediction based at least in part on data from multiple clinical applications. In certain embodiments, the prediction algorithm determines a prediction based at least in part on data from at least one clinical application and at least one medical device 120.

In certain embodiments, the notification engine 110 is adapted to generate a notification based on the determined prediction. For example, the notification may include an email to a healthcare provider treating a patient. As another example, the notification may include a message sent to an alert inbox of a physician. As another example, the notification may include a page, text message, and/or telephone message.

In certain embodiments, the notification engine 110 generates the notification based on the experience level of a medical practitioner. For example, a less experienced medical practitioner may receive a notification based on a prediction for an event that it is determined may happen in 10 minutes if unaddressed, whereas a more experienced medical practitioner may not receive such a notification. The more experienced medical practitioner may prefer to not receive such a notification if the practitioner is aware of such a trend and already plans to address the situation. If the trend continues, a notification may also be generated when an event is predicted to occur in 5 minutes. In certain embodiments, the notifications based on the predictions may be categorized. For example, notifications may be grouped into categories such as "early," "intermediate," and "danger." Such notification based on experience may be useful in a teaching hospital, for example. For example, the prediction algorithm may detect a common mistake made in a teaching environment.

Figure 2:
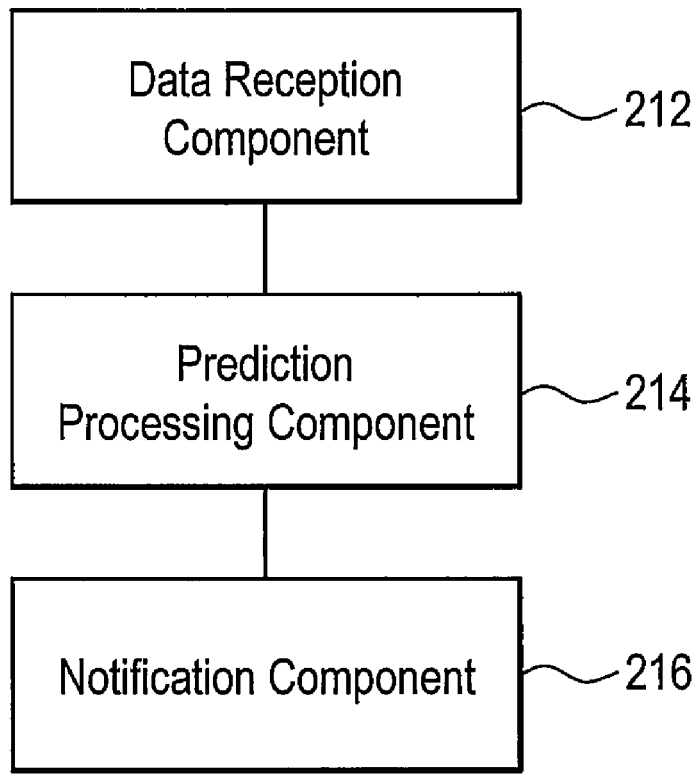
FIG. 2 illustrates a block diagram for a notification engine according to an embodiment of the present invention.

FIG. 2 illustrates a block diagram for a notification engine 210 according to an embodiment of the present invention. The notification engine 210 includes a data reception component 212, a prediction processing component 214, and a notification component 216. The notification engine 210 may be similar to the notification engine 110, discussed above, for example.

The prediction processing component 214 is in communication with the data reception component 212 and the notification component 216.

In operation, the data reception component 212 receives a sequence of data values for a parameter from a medical device. The data reception component 212 provides the parameter values to the prediction processing component 214. The prediction processing component 214 processes the parameter values to determine a prediction. Based on the prediction, the prediction processing component 214 may utilize the notification component 216 to generate a notification.

The data reception component 212 is adapted to receive a sequence of data values for at least one parameter. The data values may come from one or more medical devices similar to the medical devices 120, discussed above, for example. In certain embodiments, the data reception component 212 is adapted to receive data from one or more clinical applications.

In certain embodiments, the data reception component 212 receives the data in real-time. For example, the data reception component 212 may receive parameter data as it is generated from a medical device. In certain embodiments, the data reception component 212 receives data from a clinical data records server. That is, the data reception component 212 may receive data from an intermediate data storage infrastructure in an information system such as a clinical information system and/or a healthcare information system. The data may have been recently added to the clinical data records server, for example. Alternatively, the data may have been stored for later review and/or analysis.

In certain embodiments, the data reception component 212 may associate a time stamp with a received parameter value. For example, the data reception component 212 may form a triplet of (parameter, value, timestamp) to be provided to the prediction processing component 214. The timestamp may then be used by a prediction algorithm, for example. In certain embodiments, the received parameter value may be received with a timestamp.

The prediction processing component 214 is adapted to determine a prediction based at least in part on the parameter values received by the data reception component 212. The prediction may be determined by a predictive algorithm, for example. For example, the prediction processing component 214 may include a predictive algorithm that is executed when parameter data is received from the data reception component 212. The predictive algorithm may determine a trend based on one or more parameters. The predictive algorithm may utilize trending analysis and/or evaluating a trend over time, for example. The predictive algorithm may then determine that at some point in the future, the determined trend would indicate the occurrence of an event. Based on this determination, the prediction processing component 214 may utilize the notification component 216 to generate a notification.

The notification component 216 is adapted to generate a notification based on a prediction from the prediction processing component 214. The notification component 216 may provide a notification to a clinical information system, a healthcare information system, and/or a healthcare provider, for example. In certain embodiments, a notification is stored in a clinical server. The stored notification may be used for auditing or playback, for example.

Figure 3:
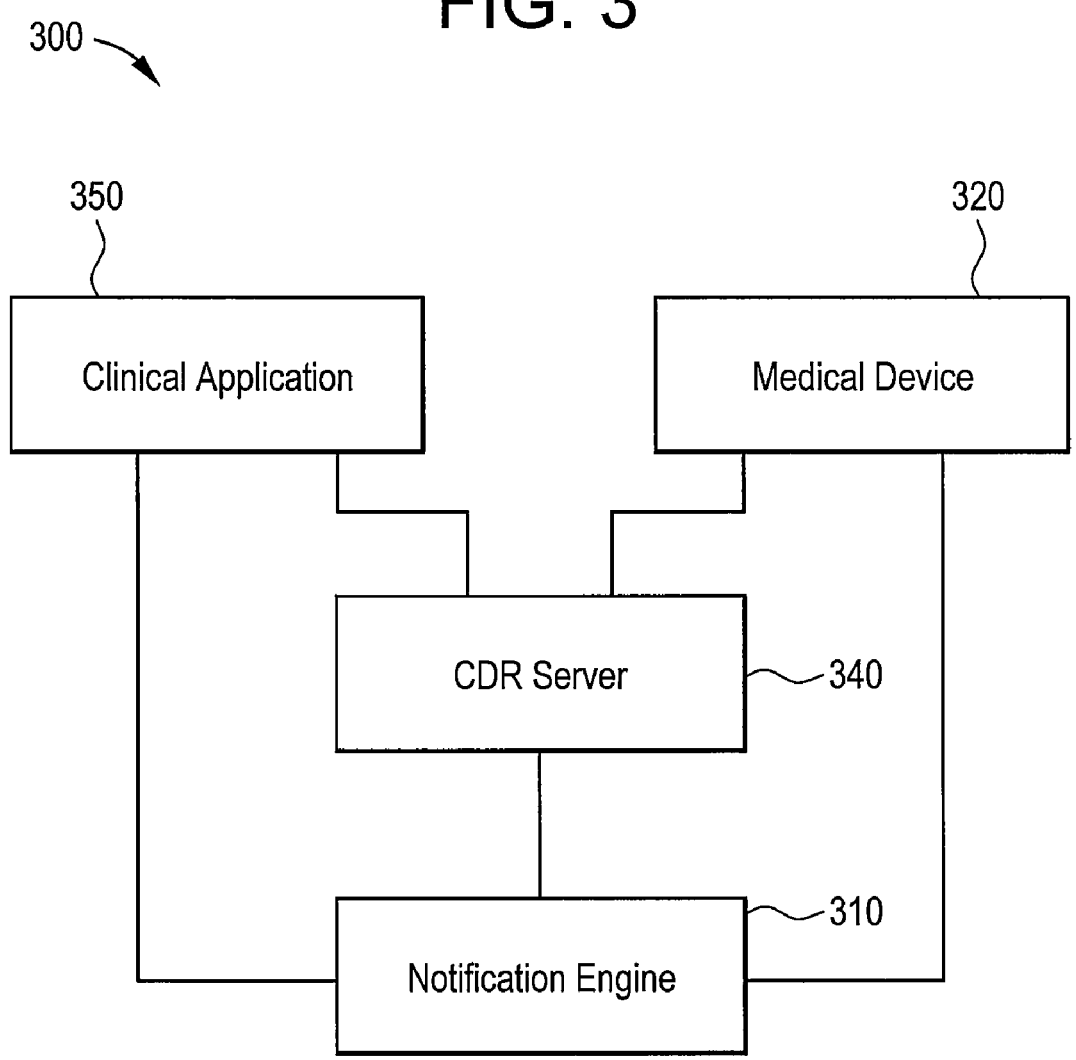
FIG. 3 illustrates a block diagram of a predictive notification system according to an embodiment of the present invention.

FIG. 3 illustrates a block diagram of a predictive notification system 300 according to an embodiment of the present invention. The system 300 includes a predictive notification engine 310, one or more medical devices 320, a clinical data record server 340, and one or more clinical applications 350.

The notification engine 310 is in communication with the clinical data record server 340. The clinical data record server 340 is in communication with the one or more medical devices 320 and the one or more clinical applications 350. In certain embodiments, the notification engine 310 is also in communication with one or more of the medical devices 320. In certain embodiments, the notification engine 310 is also in communication with one or more of the clinical applications 350.

The notification engine 310 may be similar to the notification engine 110 and/or 210, discussed above, for example. The medical devices 320 may be similar to the medical devices 120, discussed above, for example.

In operation, the clinical data record server 340 receives and stores clinical data from the medical devices 320 and/or the clinical applications 350. The notification engine 310 processes the clinical data to determine a prediction regarding the occurrence of an event. Based on the prediction, a notification is generated by the notification engine 310.

The clinical applications 350 may include an order entry application, a pharmacy application, a medication management application, an electronic medical record, and/or an anesthesia medical record keeper, for example.

The clinical data record server 340 is adapted to receive and store clinical data from one or more medical devices 320 and/or clinical applications 350. The clinical data record server 340 may be part of a clinical information system and/or a healthcare information system, for example.

The notification engine 310 is adapted to determine a prediction based at least in part on the clinical data in the clinical data record server 340. The prediction may be determined by a predictive algorithm, for example. The predictive algorithm may be similar to the predictive algorithms discussed above, for example. The notification engine 310 is adapted to generate a notification based on the determined prediction.

In certain embodiments, the notification engine 310 is adapted to receive clinical data directly from a clinical application 350. In certain embodiments, the notification engine 310 is adapted to receive clinical data directly from a medical device 320.

In certain embodiments, the predictive algorithm is specified by a user using a notification definition tool. The notification definition tool may be similar to the notification definition tool 130, discussed above, for example.

The components, elements, and/or functionality of the interface(s) and system(s) described above may be implemented alone or in combination in various forms in hardware, firmware, and/or as a set of instructions in software, for example. Certain embodiments may be provided as a set of instructions residing on a computer-readable medium, such as a memory or hard disk, for execution on a general purpose computer or other processing device, such as, for example, a PACS workstation or one or more dedicated processors.

FIG. 4 illustrates a flow diagram 400 for a method for predictive notification according to an embodiment of the present invention. The method includes the following steps, which will be described below in more detail. At step 410, data values are received. At step 420, a prediction is determined based at least in part on the data values. At step 430, a notification is generated based on the prediction. The method is described with reference to elements of systems described above, but it should be understood that other implementations are possible.

At step 410, data values are received. The data values may be a sequence of data values for one or more parameters, for example. The data values may be received from a medical device similar to the medical device 120 and/or 320, discussed above, for example.

The data values may be received at a notification engine similar to the notification engine 110, 210, and/or 310, discussed above, for example. The data values may be received by a data reception component similar to the data reception component 212, discussed above, for example.

In certain embodiments, the data values include clinical data from a clinical application. The clinical application may be similar to the clinical application 350, discussed above, for example. In certain embodiments, the data values are received from one or more clinical applications and/or medical devices.

In certain embodiments, the data values are received from a clinical data record server. The clinical data record server may be similar to the clinical data record server 340, discussed above, for example.

At step 420, a prediction is determined based at least in part on the data values. The data values may be the data values received at step 410, discussed above, for example. The prediction may be determined by a notification engine similar to the notification engine 110, 210, and/or 310, discussed above, for example. The prediction may be determined by a prediction processing component similar to the prediction processing component 214, discussed above, for example.

The prediction may be determined by a predictive algorithm, for example. For example, a predictive algorithm may be executed when the data values are received. The predictive algorithm may determine a trend based on one or more parameters. The predictive algorithm may utilize trending analysis and/or evaluating a trend over time, for example. The predictive algorithm may then determine that at some point in the future, the determined trend would indicate the occurrence of an event. Based on this determination, a notification may be provided.

In certain embodiments, the predictive algorithm is specified by a user. For example, a user may utilize a notification definition tool, similar to the notification definition tool 130, discussed above, for example, to create a predictive algorithm.

In certain embodiments, the prediction algorithm determines a prediction based at least in part on data for multiple parameters. The parameters may be from one or more medical devices, for example. In certain embodiments, the prediction algorithm determines a prediction based at least in part on data from a clinical application. In certain embodiments, the prediction algorithm determines a prediction based at least in part on data from multiple clinical applications. In certain embodiments, the prediction algorithm determines a prediction based at least in part on data from at least one clinical application and at least one medical device.

At step 430, a notification is generated based on the prediction. The prediction may be the prediction determined at step 420, discussed above, for example. The notification may be generated by a notification engine similar to the notification engine 110, 210, and/or 310, discussed above, for example. The notification may be generated by a notification component similar to the notification component 216, discussed above, for example.

The notification may include an email to a healthcare provider treating a patient, for example. As another example, the notification may include a message sent to an alert inbox of a physician.

In certain embodiments, the notification is generated based on the experience level of a medical practitioner.

Certain embodiments of the present invention may omit one or more of these steps and/or perform the steps in a different order than the order listed. For example, some steps may not be performed in certain embodiments of the present invention. As a further example, certain steps may be performed in a different temporal order, including simultaneously, than listed above.

One or more of the steps of the method may be implemented alone or in combination in hardware, firmware, and/or as a set of instructions in software, for example. Certain embodiments may be provided as a set of instructions residing on a computer-readable medium, such as a memory, hard disk, DVD, or CD, for execution on a general purpose computer or other processing device.

Thus, certain embodiments of the present invention provide systems and methods for a predictive notification engine. Certain embodiments provide notification based on information from multiple sources. Certain embodiments allow the prediction of a medical problem based on trends of the currently available variables. Certain embodiments allow multiple levels of notification based on the experience of a medical practitioner. Certain embodiments provide for user-defined notifications. Certain embodiments of the present invention provide a technical effect of a predictive notification engine. Certain embodiments provide a technical effect of notification based on information from multiple sources. Certain embodiments provide a technical effect of allowing the prediction of a medical problem based on trends of the currently available variables. Certain embodiments provide a technical effect of allowing multiple levels of notification based on the experience of a medical practitioner. Certain embodiments provide a technical effect of user-defined notifications.

Several embodiments are described above with reference to drawings. These drawings illustrate certain details of specific embodiments that implement the systems and methods and programs of the present invention. However, describing the invention with drawings should not be construed as imposing on the invention any limitations associated with features shown in the drawings. The present invention contemplates methods, systems, and program products on any machine-readable media for accomplishing its operations. As noted above, the embodiments of the present invention may be implemented using an existing computer processor, or by a special purpose computer processor incorporated for this or another purpose or by a hardwired system.

As noted above, certain embodiments within the scope of the present invention include program products comprising machine-readable media for carrying or having machine-executable instructions or data structures stored thereon. Such machine-readable media can be any available media that can be accessed by a general purpose or special purpose computer or other machine with a processor. By way of example, such machine-readable media may comprise RAM, ROM, PROM, EPROM, EEPROM, Flash, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such a connection is properly termed a machine-readable medium. Combinations of the above are also included within the scope of machine-readable media. Machine-executable instructions comprise, for example, instructions and data which cause a general purpose computer, special purpose computer, or special purpose processing machines to perform a certain function or group of functions.

Certain embodiments of the invention are described in the general context of method steps which may be implemented in one embodiment by a program product including machine-executable instructions, such as program code, for example in the form of program modules executed by machines in networked environments. Generally, program modules include routines, programs, objects, components, data structures, etc., that perform particular tasks or implement particular abstract data types. Machine-executable instructions, associated data structures, and program modules represent examples of program code for executing steps of the methods disclosed herein. The particular sequence of such executable instructions or associated data structures represent examples of corresponding acts for implementing the functions described in such steps.

Certain embodiments of the present invention may be practiced in a networked environment using logical connections to one or more remote computers having processors. Logical connections may include a local area network (LAN) and a wide area network (WAN) that are presented here by way of example and not limitation. Such networking environments are commonplace in office-wide or enterprise-wide computer networks, intranets and the Internet and may use a wide variety of different communication protocols. Those skilled in the art will appreciate that such network computing environments will typically encompass many types of computer system configurations, including personal computers, hand-held devices, multi-processor systems, microprocessor-based or programmable consumer electronics, network PCs, mini-computers, mainframe computers, and the like. Embodiments of the invention may also be practiced in distributed computing environments where tasks are performed by local and remote processing devices that are linked (either by hard-wired links, wireless links, or by a combination of hardwired or wireless links) through a communications network. In a distributed computing environment, program modules may be located in both local and remote memory storage devices.

An exemplary system for implementing the overall system or portions of the invention might include a general purpose computing device in the form of a computer, including a processing unit, a system memory, and a system bus that couples various system components including the system memory to the processing unit. The system memory may include read only memory (ROM) and random access memory (RAM). The computer may also include a magnetic hard disk drive for reading from and writing to a magnetic hard disk, a magnetic disk drive for reading from or writing to a removable magnetic disk, and an optical disk drive for reading from or writing to a removable optical disk such as a CD-ROM or other optical media. The drives and their associated machine-readable media provide nonvolatile storage of machine-executable instructions, data structures, program modules and other data for the computer.

The foregoing description of embodiments of the invention has been presented for purposes of illustration and description. It is not intended to be exhaustive or to limit the invention to the precise form disclosed, and modifications and variations are possible in light of the above teachings or may be acquired from practice of the invention. The embodiments were chosen and described in order to explain the principals of the invention and its practical application to enable one skilled in the art to utilize the invention in various embodiments and with various modifications as are suited to the particular use contemplated.

Those skilled in the art will appreciate that the embodiments disclosed herein may be applied to the formation of any healthcare information processing system. Certain features of the embodiments of the claimed subject matter have been illustrated as described herein; however, many modifications, substitutions, changes and equivalents will now occur to those skilled in the art. Additionally, while several functional blocks and relations between them have been described in detail, it is contemplated by those of skill in the art that several of the operations may be performed without the use of the others, or additional functions or relationships between functions may be established and still be in accordance with the claimed subject matter. It is, therefore, to be understood that the appended claims are intended to cover all such modifications and changes as fall within the true spirit of the embodiments of the claimed subject matter.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A system for predictive notification, the system comprising:
at least one computer processor comprising a notification engine adapted to receive a sequence of data values for a parameter from a medical device and a sequence of messages from a clinical application, wherein the notification engine is adapted to determine a prediction based at least in part on the sequence of data values and the sequence of messages, and wherein the notification engine is adapted to generate a notification based on the prediction and an experience level for a user.

2. The system of claim 1, wherein the notification engine is adapted to receive a second sequence of data values for a second parameter.

3. The system of claim 2, wherein the second sequence is from a second medical device.

4. The system of claim 2, wherein the second sequence is from the same medical device.

5. The system of claim 2, wherein the prediction is further based at least in part on the second sequence of data values.

6. The system of claim 1, wherein each data value in the sequence is associated with a timestamp.

7. The system of claim 1, wherein the prediction is based on a determination of a trend in the sequence.

8. The system of claim 1, wherein a second notification is generated based on a second prediction determined based at least in part on the sequence of data values and subsequent data values for the parameter, wherein the second notification is generated after the first notification, and wherein the second notification is generated when the second prediction indicates that a previously detected condition has not been corrected.

9. The system of claim 1, wherein the prediction is determined by detecting a common mistake made in a teaching environment.

10. A method for predictive notification, the method comprising:
performing by one or more computer processors, at least:
receiving a sequence of data values for a parameter from a medical device; receiving a sequence of messages from a clinical application;
determining a prediction based at least in part on the sequence of data values and the sequence of messages; and
generating a notification based on the prediction and an experience level for a user.

11. The method of claim 10, further including receiving a second sequence of data values for a second parameter.

12. The method of claim 11, wherein the second sequence is from a second medical device.

13. The method of claim 11, wherein the second sequence is from the same medical device.

14. The method of claim 11, wherein the prediction is further based at least in part on the second sequence of data values.

15. The method of claim 10, wherein the prediction is based on a determination of a trend in the sequence.

16. A non-transitory computer-readable medium including a set of instructions for execution on a computer, the set of instructions comprising:

a data reception routine configured to receive a sequence of data values for a parameter from a medical device;
a message reception routine configured to receive a sequence of messages from a clinical application;
a prediction processing routine configure to determine a prediction based at least in part on the sequence of data values and the sequence of messages; and
a notification routine configured to generate a notification based on the prediction and an experience level for a user.

* * * * *